United States Patent
Tsujita

(10) Patent No.: US 9,888,856 B2
(45) Date of Patent: Feb. 13, 2018

(54) PHOTOACOUSTIC IMAGE GENERATION APPARATUS, SYSTEM AND METHOD

(71) Applicant: FUJIFILM Corporation, Tokyo (JP)

(72) Inventor: Kazuhiro Tsujita, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 127 days.

(21) Appl. No.: 14/535,735

(22) Filed: Nov. 7, 2014

(65) Prior Publication Data
US 2015/0057534 A1 Feb. 26, 2015

Related U.S. Application Data

(63) Continuation of application No. PCT/JP2013/002912, filed on May 2, 2013.

(30) Foreign Application Priority Data

May 8, 2012 (JP) .................. 2012-106398

(51) Int. Cl.
A61B 5/00 (2006.01)

(52) U.S. Cl.
CPC .......... A61B 5/0095 (2013.01); A61B 5/7235 (2013.01); A61B 5/7425 (2013.01)

(58) Field of Classification Search
CPC ............... A61B 4/0095; A61B 4/055
(Continued)

(56) References Cited

U.S. PATENT DOCUMENTS 6,146,330 A 11/2000 Tujino et al.
7,095,505 B1 * 8/2006 Beard .................. A61B 5/0059
356/502
(Continued)

FOREIGN PATENT DOCUMENTS

JP 11-290318 A 10/1999
JP 2004-73620 A 3/2004
(Continued)

OTHER PUBLICATIONS

Chinese Office Action, dated Oct. 30, 2015, for corresponding Chinese Application No. 201380024286.0, with an English translation.
(Continued)

Primary Examiner — Tse Chen
Assistant Examiner — Joanne Hoffman
(74) Attorney, Agent, or Firm — Birch, Stewart, Kolasch & Birch, LLP

(57) ABSTRACT

A photoacoustic wave induced in a subject to be examined by illumination of the subject to be examined with light is detected. A first photoacoustic image corresponding to a frequency component less than or equal to a predetermined frequency and a second photoacoustic image corresponding to a frequency component higher than a predetermined frequency are generated based on a detection signal of the detected photoacoustic wave. The first photoacoustic image and the second photoacoustic image are combined together by placing, on a pixel in the first photoacoustic image the pixel value of which is less than or equal to a threshold, a pixel in the second photoacoustic image corresponding to the pixel in the first photoacoustic image.

11 Claims, 5 Drawing Sheets

(58) Field of Classification Search
USPC .......................................................... 600/407
See application file for complete search history.

(56) References Cited

U.S. PATENT DOCUMENTS

| | | | | |
|---|---|---|---|---|
| 2003/0187319 | A1* | 10/2003 | Kaneko | A61N 2/00 600/9 |
| 2005/0187471 | A1 | 8/2005 | Kanayama et al. | |
| 2008/0177183 | A1* | 7/2008 | Courtney | A61B 5/0062 600/463 |
| 2010/0322497 | A1* | 12/2010 | Dempsey | G01R 33/4826 382/131 |
| 2011/0066023 | A1 | 3/2011 | Kanayama et al. | |
| 2012/0253173 | A1* | 10/2012 | Endo | G06T 11/008 600/411 |
| 2014/0350358 | A1* | 11/2014 | Oikawa | A61B 5/743 600/301 |

FOREIGN PATENT DOCUMENTS

| | | |
|---|---|---|
| JP | 2005-218684 A | 3/2004 |
| JP | 2004-351023 A | 12/2004 |
| JP | 2009-119134 A | 6/2009 |

OTHER PUBLICATIONS

Calasso et al., "Photoacoustic Point Source", Physical Review Letters, vol. 86, No. 16, Apr. 16, 2001, pp. 3550-3553.
International Search Report for PCT/JP2013/002912 dated Jun. 25, 2013.
Written Opinion of the International Seaching Authority for PCT/JP2013/002912 dated Jun. 25, 2013.
Zhang et al., "Deconvolution reconstruction of full-view and limited-view photoacoustic tomography: a simulation study", J. Opt. Soc. Am. A, vol. 25, No. 10, Oct. 2008, pp. 2436-2443.

* cited by examiner

PHOTOACOUSTIC IMAGE GENERATION APPARATUS, SYSTEM AND METHOD

CROSS-REFERENCE TO RELATED APPLICATIONS

This application is a Continuation of PCT International Application No. PCT/JP2013/002912 filed on May 2, 2013, which claims priority under 35 U.S.C. § 119(a) to Japanese Patent Application No. 2012-106398 filed on May 8, 2012. Each of the above applications is hereby expressly incorporated by reference, in its entirety, into the present application.

BACKGROUND OF THE INVENTION

Field of the Invention

The present invention relates to a photoacoustic image generation apparatus, system and method, and particularly to a photoacoustic image generation apparatus, system and method in which light is output to a subject to be examined, and an acoustic wave induced in the subject to be examined by illumination with the light is detected, and a photoacoustic image is generated.

Description of the Related Art

Ultrasonography is known as one of image examination methods that can perform non-invasive examination to find the state of the inside of a living body. In ultrasonography, an ultrasonic probe that can send and receive ultrasound is used. When ultrasound is sent from the ultrasonic probe to the subject to be examined (living body), the ultrasound travels in the living body and is reflected at a tissue interface in the living body. The reflected ultrasound is received by the ultrasonic probe. It is possible to image the state of the inside of the subject to be examined by calculating a distance based on time till the reflected ultrasound returns to the ultrasonic probe.

Further, photoacoustic imaging, which images the inside of a living body by utilizing photoacoustic effects, is known. Generally, pulsed laser light is output to the inside of the living body in photoacoustic imaging. In the inside of the living body, living tissue absorbs energy of the pulsed laser light, and ultrasound (photoacoustic signals) is induced by adiabatic expansion caused by the energy. The photoacoustic signals are detected by an ultrasonic probe or the like, and a photoacoustic image is constructed based on the detection signals. Accordingly, it is possible to visualize the inside of the living body based on the photoacoustic signals.

Meanwhile, in ultrasonic imaging, harmonic imaging is known. In harmonic imaging, the frequency of ultrasound sent into the subject to be examined is regarded as a fundamental frequency, and ultrasound with frequency of an integer multiple of the fundamental frequency (harmonics) is detected. Further, an ultrasonic image is generated based on the detected harmonics. Regarding harmonic imaging, Japanese Unexamined Patent Publication No. 2004-073620 (Patent Document 1) discloses generation of a fundamental frequency image based on a fundamental frequency, and generation of a harmonic image based on harmonics, and display of the fundamental frequency image and the harmonic image that are combined together by addition. Further, Japanese Unexamined Patent Publication No. 11 (1999)-290318 (Patent Document 2) discloses the feature that a fundamental frequency image and a harmonic image are partially combined together so that a region of interest is composed of a harmonic image and the other region is composed of a fundamental frequency image.

SUMMARY OF THE INVENTION

A photoacoustic image includes various frequency components from a low frequency component through a high frequency component. For example, when blood vessels are displayed, if display of only low frequency components is considered, large-diameter blood vessels are easily observable. However, infatuation about details is lost. In contrast, if display of only high frequency components is considered, fragmentation of the blood vessels becomes noticeable. If an image of high frequency components is simply placed on an image of low frequency components, the fragmented blood vessels are superposed on the large-diameter blood vessels. Therefore, an image in which bright fragments are scattered is generated, and observation of such an image is difficult.

In view of the foregoing circumstances, it is an object of the present invention to provide a photoacoustic image generation apparatus, system and method that can combine an image of low frequency components and an image of high frequency components together in such a manner that the degree of difficulty in observation is suppressed, compared with a case of simply placing the image of low frequency components and the image of high frequency components one on the other.

To achieve the aforementioned object, the present invention provides a photoacoustic image generation apparatus including an image generation means that generates photoacoustic images based on a detection signal of a photoacoustic wave induced in a subject to be examined by illumination of the subject to be examined with light, and which generates a first photoacoustic image corresponding to a frequency component less than or equal to a predetermined frequency and a second photoacoustic image corresponding to a frequency component higher than a predetermined frequency, and an image combination means that combines the first photoacoustic image and the second photoacoustic image together by placing, on a pixel in the first photoacoustic image the pixel value of which is less than or equal to a threshold, a pixel in the second photoacoustic image corresponding to the pixel in the first photoacoustic image.

The present invention may adopt a structure in which the image generation means includes an original image generation means that generates, based on the detection signal of the photoacoustic wave, a third photoacoustic image including both of the component of less than or equal to the predetermined frequency and the component of higher than the predetermined frequency, a first filter means that generates the first photoacoustic image by applying a low-pass filter that at least attenuates a component of higher than the predetermined frequency to the third photoacoustic image, and a second filter means that generates the second photoacoustic image by applying a high-pass filter that at least attenuates a component of less than or equal to the predetermined frequency to the third photoacoustic image.

The original image generation means may obtain, from three-dimensional image data based on a three-dimensionally detected photoacoustic wave, a cross section by cutting along a plane perpendicular to one of axes constituting three-dimensional space, and generate, as the third photoacoustic image, a tomographic image in which image data in a predetermined range in a direction along the one of the axes are combined, and the predetermined range including the cross section obtained by cutting.

In the above case, the original image generation means may generate plural tomographic images by obtaining cross sections by cutting at plural positions along the one of the axes. In that case, the original image generation means may obtain the cross sections by cutting at regular intervals.

The original image generation means may obtain, along one of the axes corresponding to a depth direction of the subject to be examined, the cross section or the cross sections by cutting in a direction parallel to a photoacoustic wave detection surface during detection of the photoacoustic wave.

The original image generation means may combine the image data in the predetermined range by projecting a maximum value of the image data in the predetermined range or by calculating the integral of the image data in the predetermined range.

The image combination means may combine the first photoacoustic image and the second photoacoustic image after assigning different colors to them.

The photoacoustic image generation apparatus of the present invention may further include a deconvolution that deconvolutes, from the detection signal of the photoacoustic wave, a differential waveform of the light with which the subject to be examined has been illuminated.

Further, the present invention provides a photoacoustic image generation system including a light source that outputs light with which a subject to be examined is illuminated, a photoacoustic wave detection means that detects a photoacoustic wave induced in the subject to be examined by illumination of the subject to be examined with the light, an image generation means that generates photoacoustic images based on a detection signal of the detected photoacoustic wave, and which generates a first photoacoustic image corresponding to a frequency component less than or equal to a predetermined frequency and a second photoacoustic image corresponding to a frequency component higher than a predetermined frequency, and an image combination means that combines the first photoacoustic image and the second photoacoustic image together by placing, on a pixel in the first photoacoustic image the pixel value of which is less than or equal to a threshold, a pixel in the second photoacoustic image corresponding to the pixel in the first photoacoustic image.

Further, the present invention provides a photoacoustic image generation method including the step of generating photoacoustic images based on a detection signal of a photoacoustic wave induced in a subject to be examined by illumination of the subject to be examined with light, wherein a first photoacoustic image corresponding to a frequency component less than or equal to a predetermined frequency and a second photoacoustic image corresponding to a frequency component higher than a predetermined frequency are generated, and the step of combining the first photoacoustic image and the second photoacoustic image together by placing, on a pixel in the first photoacoustic image the pixel value of which is less than or equal to a threshold, a pixel in the second photoacoustic image corresponding to the pixel in the first photoacoustic image.

The photoacoustic image generation apparatus, system and method of the present invention generates a first photoacoustic image including a low frequency component and a second photoacoustic image including a high frequency component, and combines the first photoacoustic image and the second photoacoustic image together by placing, on a pixel in the first photoacoustic image the pixel value of which is less than or equal to a threshold, a pixel in the second photoacoustic image corresponding to the pixel in the first photoacoustic image. The pixel in the first photoacoustic image the pixel value of which is less than or equal to the threshold corresponds to a pixel without information or with a small amount of information in the image of low frequency components. Therefore, it is possible to compensate a part without information or with the small amount of information in the first photoacoustic image with information about the second photoacoustic image by placing, on the pixel in the first photoacoustic image, the pixel in the second photoacoustic image corresponding to such a pixel. Further, it is possible to suppress the degree of difficulty in observation, compared with a case of simply placing the image of low frequency components and the image of high frequency components one on the other, by combining the images as described above.

DESCRIPTION OF THE PREFERRED EMBODIMENTS

Figure 1:
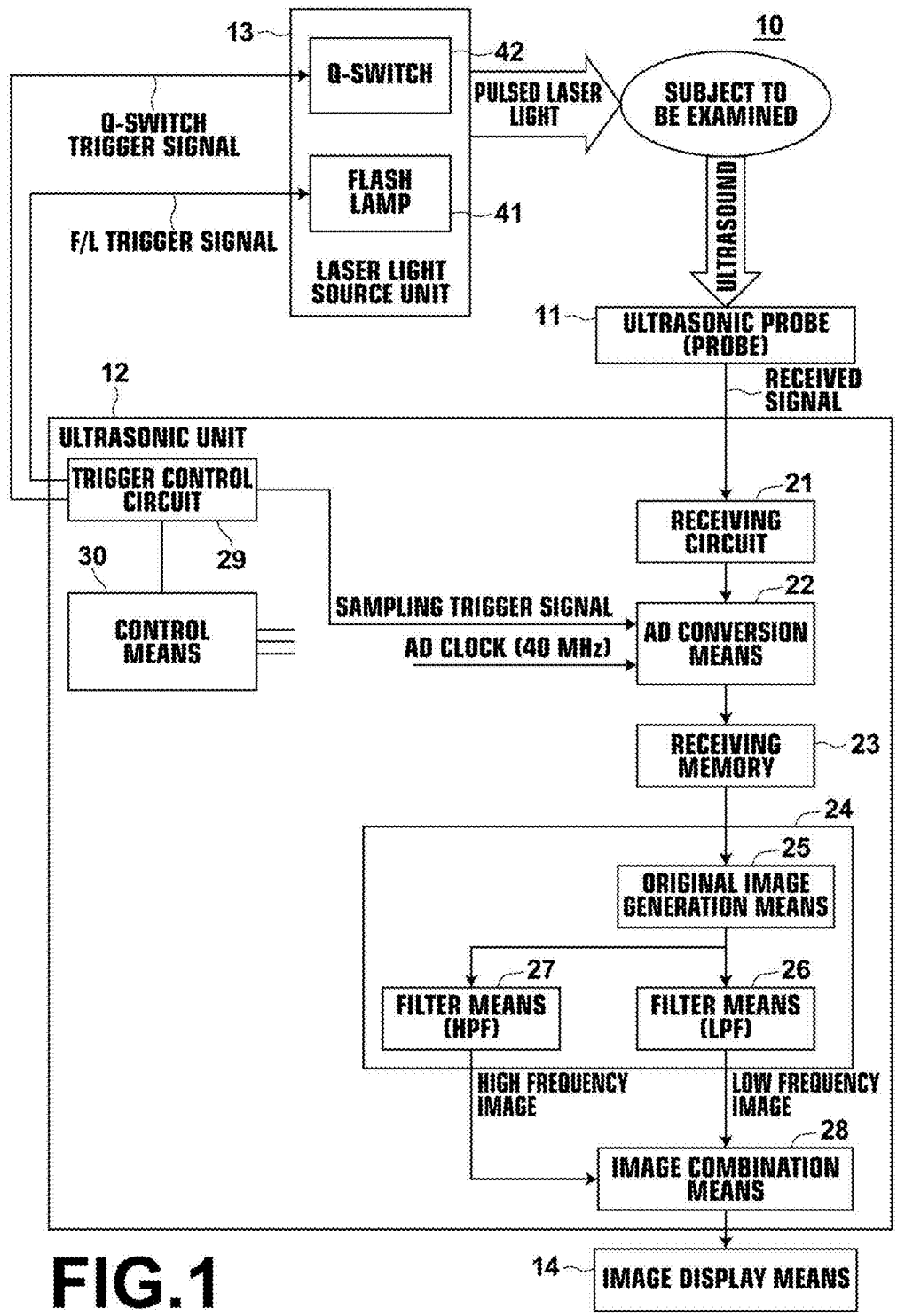
FIG. 1 is a block diagram illustrating a photoacoustic image generation system according to a first embodiment of the present invention.

Hereinafter, embodiments of the present invention will be described in detail with reference to the drawings. FIG. 1 is a diagram illustrating a photoacoustic image generation system according to a first embodiment of the present invention. A photoacoustic image generation system (photoacoustic image diagnosis system) 10 includes an ultrasonic probe (probe) 11, an ultrasonic unit 12, and a laser unit 13.

The laser unit 13 is a light source, and generates light (laser light) output to a subject to be examined. The wavelength of the laser light should be appropriately set based on a target of observation. The laser unit 13 outputs light, for example, with a wavelength at which absorption by hemoglobin is high, and which is specifically a wavelength of 750 nm or 800 nm. The laser light output from the laser unit 13 is guided to the probe 11 by a light guide means, for example, such as an optical fiber, and is output from the probe 11 to the subject to be examined. Alternatively, the laser light may be output to the subject to be examined from a position other than the probe 11.

The probe 11 includes an acoustic wave detection means that detects acoustic waves (ultrasound) output from the inside of the subject to be examined. The probe 11 includes plural ultrasonic transducers, for example, linearly arranged. The probe 11 detects, by the plural ultrasonic transducers, photoacoustic waves induced by absorption of light output from the laser unit 13 by the target of measurement in the subject to be examined.

The ultrasonic unit 12 corresponds to a photoacoustic image generation apparatus that generates a photoacoustic image based on detected photoacoustic waves. The ultrasonic unit 12 includes a receiving circuit 21, an AD conversion means 22, a receiving memory 23, an image generation means 24, an image combination means 28, a trigger control circuit 29, and a control means 30. The control means 30 controls each unit in the ultrasonic unit 12. The receiving circuit 21 receives detection signals of photoacoustic waves (photoacoustic signals) detected by the probe 11. The AD conversion means 22 performs sampling on the photoacoustic signals received by the receiving circuit 21, and converts the photoacoustic signals into digital signals. The AD conversion means 22 performs sampling on the photoacoustic signals at a predetermined cycle of sampling, for example, synchronized with an AD clock signal.

The trigger control circuit 29 outputs a light trigger signal, which instructs the laser unit 13 to output light. The laser unit 13 includes a flash lamp 41 that excites a laser medium, such as YAG or titanium-sapphire, which is not illustrated, and a Q-switch 42 that controls oscillation of the laser. When the trigger control circuit 29 outputs a flash lamp trigger signal, the laser unit 13 turns on the flash lamp 41, and the laser medium is excited. For example, when the flash lamp 41 has sufficiently excited the laser medium, the trigger control circuit 29 outputs a Q-switch trigger signal. The Q-switch 42 is turned on when the Q-switch trigger signal is received, and laser light is output from the laser unit 13. A time period needed for the laser medium to become sufficiently excited after the flash lamp 41 is turned on may be estimated based on the properties of the laser medium, and the like.

The Q-switch 42 may be turned on in the laser unit 13 after the laser medium is sufficiently excited, instead of controlling the Q-switch from the trigger control circuit 29. In that case, a signal indicating that the Q-switch 42 has been turned on may be sent to the ultrasonic unit 12 to notify that. Here, the term "light trigger signal" represents a concept including at least one of the flash lamp trigger signal and the Q-switch trigger signal. When the Q-switch trigger signal is output from the trigger control circuit 29, the Q-switch trigger signal corresponds to the light trigger signal. When timing of the Q-switch trigger is generated in the laser unit 13, the flash lamp trigger signal may correspond to the light trigger signal. When the light trigger signal is output, the laser light is output to the subject to be examined, and the photoacoustic signals are detected.

Further, the trigger control circuit 29 outputs a sampling trigger signal to instruct the AD conversion means 22 to start sampling. The trigger control circuit 29 outputs the sampling trigger signal at predetermined timing after output of the light trigger signal. The trigger control circuit 29 outputs the sampling trigger signal after output of the light trigger signal, desirably, at timing of actually outputting laser light to the subject to be examined. For example, the trigger control circuit 29 outputs the sampling trigger signal synchronized with output of the Q-switch trigger signal.

When the AD conversion means 22 receives the sampling trigger signal, the AD conversion means 22 starts sampling on the photoacoustic signals detected by the probe 11. The AD conversion means 22 stores the sampled photoacoustic signals in the receiving memory 23. As the receiving memory 23, for example, a semiconductor storage device may be used. Alternatively, other types of storage device, such as a magnetic storage device, may be used as the receiving memory 23.

The image generation means 24 reads out photoacoustic signals from the receiving memory 23, and generates a photoacoustic image based on the readout photoacoustic signals. The image generation means 24 generates a first photoacoustic image (a low frequency image) corresponding to a frequency component less than or equal to a predetermined frequency (a low frequency component) and a second photoacoustic image (a high frequency image) corresponding to a frequency component higher than a predetermined frequency (a high frequency component). It is not necessary that the frequency band of the first photoacoustic image and the frequency band of the second photoacoustic image are completely separated from each other. In other words, the frequency bands may partially overlap.

The image generation means 24 includes, for example, a original image generation means 25, a first filter means 26, and a second filter means 27. The original image generation means 25 generates, based on photoacoustic signals stored in the receiving memory 23, a photoacoustic image (a third photoacoustic image) including both of the low frequency component and the high frequency component. Generation of a photoacoustic image typically includes reconstruction of photoacoustic signals, wave detection and logarithmic conversion and construction of the photoacoustic image.

The original image generation means 25 reconstructs the photoacoustic signals, for example, by using a delay-and-sum method (which is synonymous with Delay and Sum, phase matching addition and phasing addition). For example, the original image generation means 25 adds photoacoustic signals for 64 elements together at delay time corresponding to the position of each of the elements (each of ultrasonic transducers). When the delay-and-sum method is carried out, sound speed in the subject to be examined may be assumed to be constant. Alternatively, the distribution of sound speeds may be taken into consideration, and the delay time of each element may be corrected. Instead of the delay-and-sum method, a Hough transform method or a Fourier transform method may be used to perform reconstruction.

The original image generation means 25 performs wave detection and logarithmic transform on the reconstructed photoacoustic signals, and generates a photoacoustic image based on data of each line on which logarithmic transform has been performed. The original image generation means 25 generates a photoacoustic image (a third photoacoustic image), for example, by transforming the position of a photoacoustic signal (peak part) in the direction of a time axis to a position in a depth direction in a tomographic image.

For example, the original image generation means 25 may generate three-dimensional image data based on three-dimensionally detected photoacoustic signals. Further, the original image generation means 25 may generate, based on the three-dimensional image data, a tomographic image (a third photoacoustic image) representing an arbitrary cross section. The original image generation means 25 obtains three-dimensional image data by cutting, for example, along a plane perpendicular to one of axes constituting three-dimensional space. The original image generation means 25 generates, as the third photoacoustic image, a tomographic image data in which image data in a predetermined range in a direction perpendicular to the cross section are combined, and the predetermined range including the cross section obtained by cutting. For example, when the original image generation means 25 obtains a cross section at a position on an axis corresponding to the depth direction of the subject to be examined by cutting along a plane parallel to an acoustic wave detection surface of the probe 11, the original image generation means 25 combines a predetermined number of tomographic images located on the front side and the rear side of the cross section (toward a shallow direction and toward a deep direction) into an image. The original image generation means 25 combines the image data in the predetermined range into data of one image, for example, by projecting a maximum value of image data in the predetermined range. Alternatively, the image data in the predetermined range may be combined by calculating the integral (an average) of the image data in the predetermined range.

The first filter means 26 generates the first photoacoustic image corresponding to a low frequency component by applying a low-pass filter (LPF) to the third photoacoustic image generated by the original image generation means 25. The low-pass filter at least attenuates a component of higher than a predetermined frequency. The second filter means 27 generates the second photoacoustic image corresponding to a high frequency component by applying a high-pass filter to the third photoacoustic image generated by the original image generation means 25. The high-pass filter at least attenuates a component of less than or equal to a predetermined frequency.

The image combination means 28 combines the first photoacoustic image (a low frequency image) and the second photoacoustic image (a high frequency image) into an image. Specifically, the image combination means 28 combines the low frequency image and the high frequency image together by placing, on a pixel in the low frequency image the pixel value of which is less than or equal to a threshold, a pixel in the high frequency image corresponding to the pixel in the low frequency image. The pixel in the low frequency image the pixel value of which is less than or equal to the threshold corresponds to a pixel without information about a low frequency component. The image combination means 28 combines the low frequency image and the high frequency image into an image based on the low frequency image in such a manner that a part of the low frequency image without information is compensated by the high frequency image. The combined image, which has been combined by the image combination means 28, is displayed on a display screen of an image display means 14, such as a display device. The low frequency image and the high frequency image may be displayed together in addition to the combined image.

Figure 2:
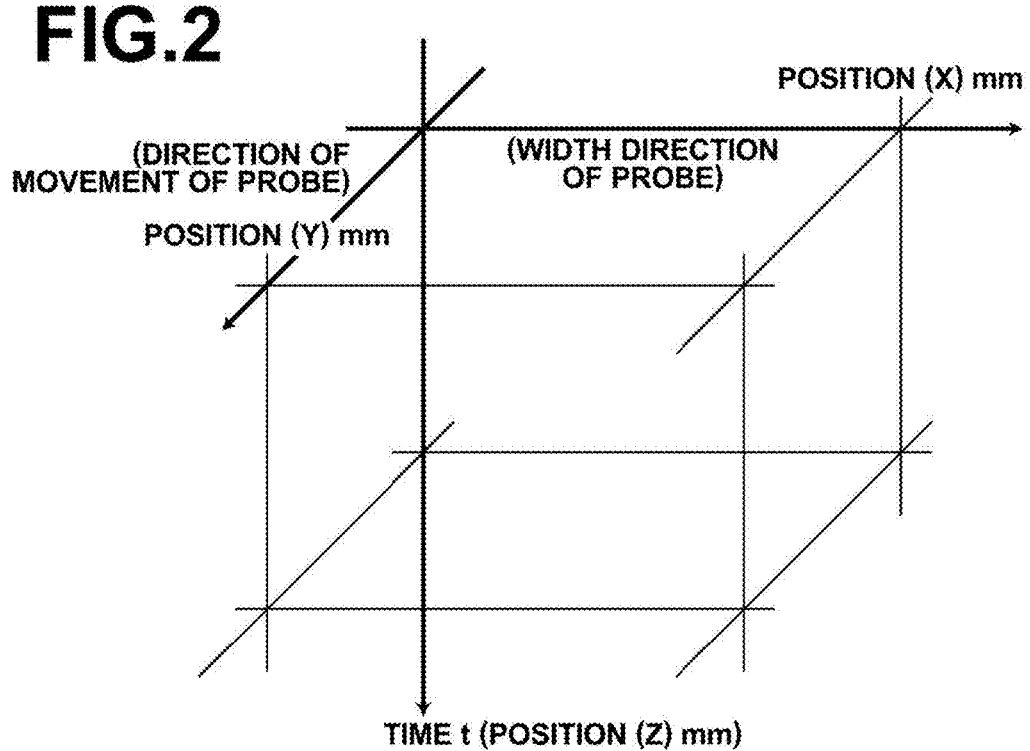
FIG. 2 is a diagram illustrating photoacoustic signal detection space.

FIG. 2 is a diagram illustrating photoacoustic signal detection space. The direction of a time axis of photoacoustic signals corresponds to the depth direction (Z direction) of a photoacoustic image. The probe 11 includes plural detector elements (ultrasonic transducers), for example, linearly arranged in X direction. Photoacoustic signals are three-dimensionally obtainable by making such a probe 11 scan in Y direction. Instead of making the probe in which the plural detector elements are linearly arranged scan, a probe in which plural detector elements are two-dimensionally arranged in X direction and Y direction may be used. In this case, photoacoustic signals are three-dimensionally obtainable without making the probe scan.

Figure 3:
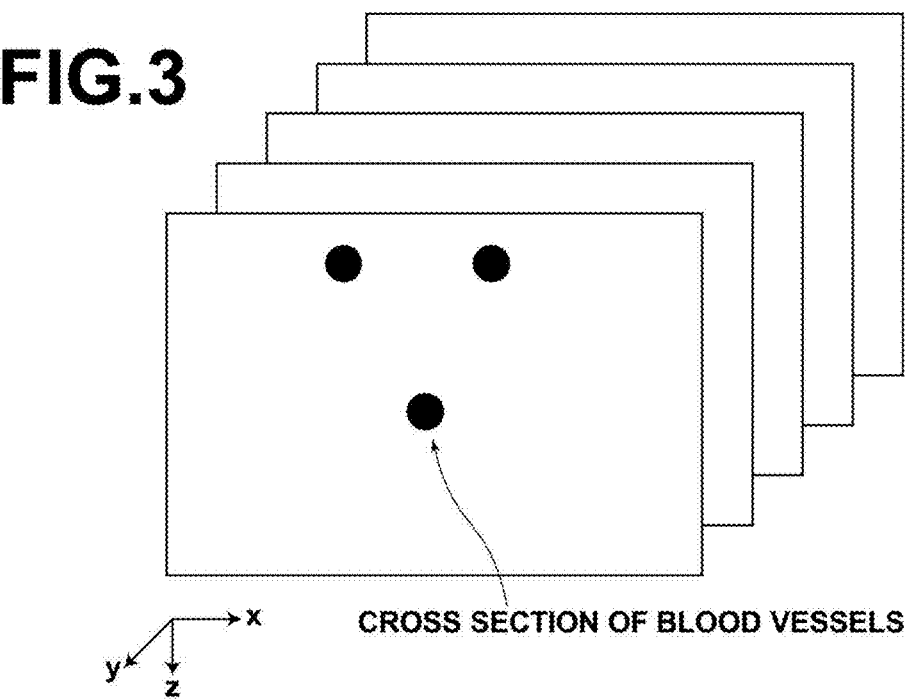
FIG. 3 is a diagram illustrating tomographic images of XZ cross sections.

FIG. 3 is a diagram illustrating tomographic images (photoacoustic images) of XZ cross sections. For example, when the probe 11 includes plural ultrasonic transducers arranged in X direction and the probe 11 scans in Y direction, a photoacoustic image of an XZ cross section is generated at each scan position. For example, if a blood vessel transversally runs in Y direction, a circular cross section of a blood vessel appears in a photoacoustic image of the XZ cross section. When plural photoacoustic images of XZ cross sections at respective scan positions are connected to each other in Y direction, three-dimensional photoacoustic image data are obtainable.

Figure 4:
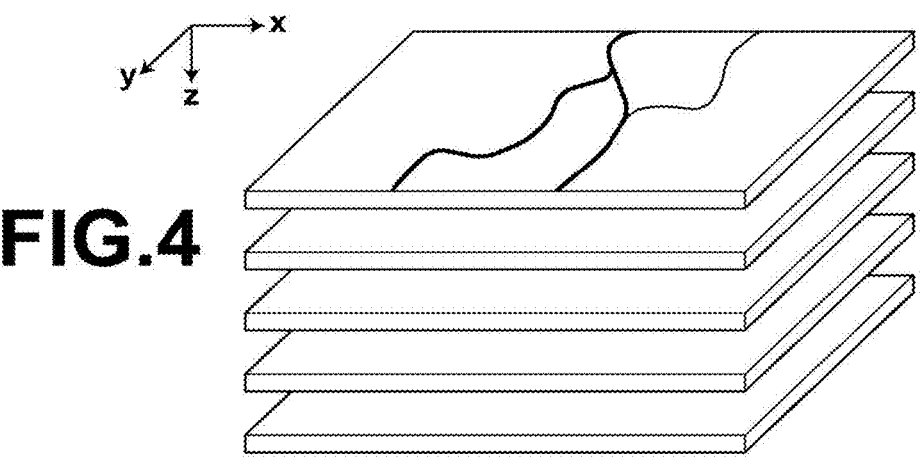
FIG. 4 is a diagram illustrating tomographic images generated by a tomographic image generation means.

FIG. 4 is a diagram illustrating a third photoacoustic image generated by the original image generation means 25. The original image generation means 25 obtains, for example along Z-axis, cross sections in planes (XY planes) parallel to the photoacoustic detection surface of the probe 11 by cutting from three-dimensional photoacoustic data, and generates tomographic image data (a third photoacoustic image) in which image data for a predetermined number of cross sections are combined. For example, the original image generation means 25 generates the third photoacoustic image by projecting a maximum value of image data of plural cross sections, for example, corresponding to 2 mm in the depth direction (Z direction). The original image generation means 25 obtains cross sections by cutting at plural positions located at regular intervals, for example, along Z-axis, and generates a third photoacoustic image for every 2 mm. It is not necessary that the third photoacoustic image generated by the original image generation means 25 is a tomographic image parallel to XY plane. The third photoacoustic image may be a tomographic image parallel to XZ plane or YZ plane.

Figure 5:
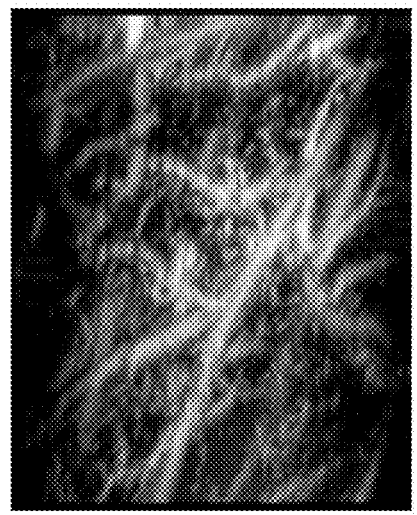
FIG. 5 is a diagram illustrating an image example of a tomographic image.

FIG. 5 is a diagram illustrating an actual example of a third photoacoustic image. The image illustrated in FIG. 5 corresponds to image data of one of plural cross sections illustrated in FIG. 4. The photoacoustic image illustrated in FIG. 5 includes all of frequency components from a low frequency component through a high frequency component. Therefore, it is difficult to recognize which part of the image represents a blood vessel.

Figure 6:
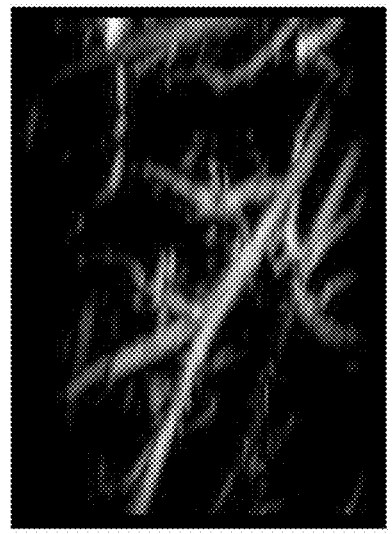
FIG. 6 is a diagram illustrating an image example of a first photoacoustic image.

FIG. 6 is a diagram illustrating an image (a first photoacoustic image) constructed from a low frequency component in the third photoacoustic image illustrated in FIG. 5. The first photoacoustic image (the low frequency image) illustrated in FIG. 6 is obtainable by applying a filter that at least attenuates a high frequency component to the third photoacoustic image illustrated in FIG. 5. In FIG. 6, a frequency component of 5 MHz or less in the third photoacoustic image is imaged. When the low frequency component is imaged, it is possible to easily observe a blood vessel with a specific diameter, compared with the third photoacoustic image illustrated in FIG. 5. However, information about details is lost in the low frequency image.

Figure 7:
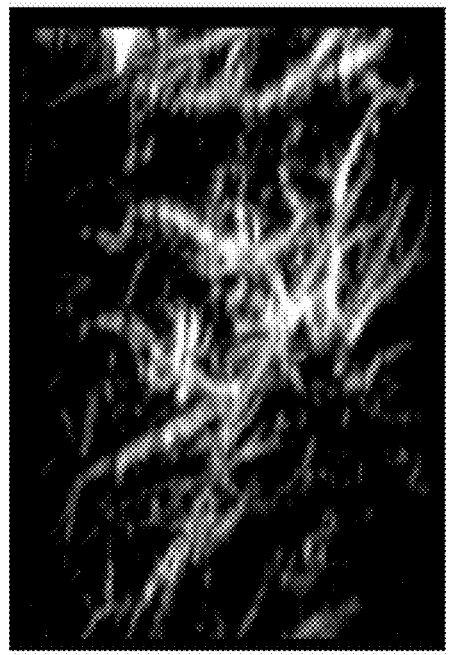
FIG. 7 is a diagram illustrating an image example of a second photoacoustic image.

FIG. 7 is a diagram illustrating an image (a second photoacoustic image) constructed from a high frequency component in the third photoacoustic image illustrated in FIG. 5. The second photoacoustic image (the high frequency image) illustrated in FIG. 7 is obtainable by applying a filter that at least attenuates a low frequency component to the third photoacoustic image illustrated in FIG. 5. In FIG. 7, a frequency component of 5 MHz or higher in the third photoacoustic image is imaged. When the high frequency component is imaged, an image including a large amount of information about details is obtainable. However, fragmentation of a large-diameter blood vessel occurs.

Figure 8:
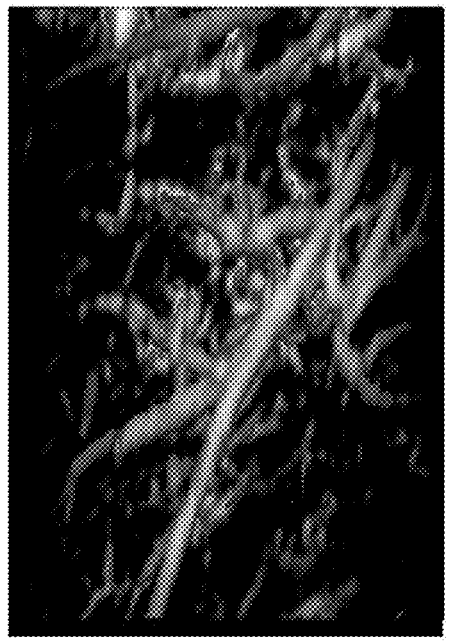
FIG. 8 is a diagram illustrating an image example of a combined image.

FIG. 8 is a combination image of the low frequency image and the high frequency image. The combination image illustrated in FIG. 8 is obtainable by placing, on a part with a pixel value less than or equal to a threshold in the low frequency image, a corresponding part of the high frequency image. Information about details that are lost in the low frequency image illustrated in FIG. 6 is compensated by information about the high frequency image illustrated in FIG. 7. Therefore, observation of blood vessels with relatively small diameters becomes possible. When the aforementioned combination method is adopted in this manner, it is possible to observe a blood vessel with a specific diameter without losing information about details.

In the above descriptions, 5 MHz is set as a boundary between the low frequency and the high frequency. This frequency is appropriate to observe a blood vessel with a diameter of about 0.5 mm in the low frequency image. The boundary between the low frequency and the high frequency should be appropriately set based on the diameter of a blood vessel to be observed. For example, the diameter of a blood vessel to be observed may be determined based on a region to be measured. Further, a cut-off frequency of the low-pass filter in the first filter means 26 (FIG. 1) and a cut-off frequency of the high-pass filter in the second filter means 27 may be set based on the determined diameter of the blood vessel. Alternatively, a user may select the diameter of a blood vessel to be observed, and the frequency of filtering may be set based on the selected diameter.

Figure 9:
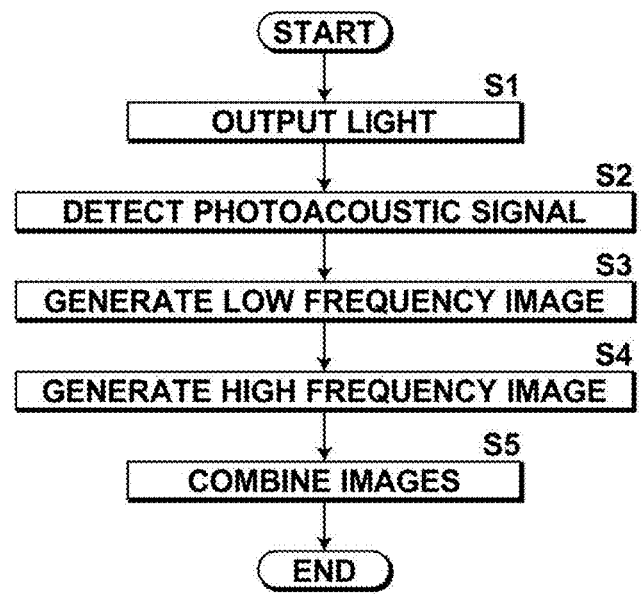
FIG. 9 is a flow chart of an operation procedure of the photoacoustic image generation system.

Next, operation procedures will be described. FIG. 9 shows the operation procedures of the photoacoustic image generation system 10. The trigger control circuit 29 outputs a flash lamp trigger signal to the laser unit 13. In the laser unit 13, the flash lamp 41 is turned on in response to the flash lamp trigger signal, and laser medium begins to be excited. The trigger control circuit 29 makes the laser unit 13 output pulsed laser light by sending a Q-switch trigger signal to the laser unit 13 to turn on the Q-switch 42 (step S1). The trigger control circuit 29 outputs the Q-switch trigger signal, for example, at timing having predetermined temporal relationship with timing of outputting the flash lamp trigger signal. The trigger control circuit 29 outputs the Q-switch trigger signal, for example, 150 µs after the flash lamp has output light.

The laser light output from the laser unit 13 illuminates the subject to be examined. In the subject to be examined, photoacoustic signals are induced by the pulsed laser light that has illuminated the subject to be examined. The probe 11 detects the photoacoustic signals induced in the subject to be examined (step S2). The photoacoustic signals detected by the probe are input to the AD conversion means 22 through the receiving circuit 21. The AD conversion means 22 performs sampling on the photoacoustic signals, and converts them into digital data, and stores the digital data in the receiving memory 23. Three-dimensional data of photoacoustic signals are obtainable, for example, by outputting light and detecting photoacoustic signals at plural scan positions while making the probe 11, in which plural ultrasonic transducers are linearly arranged, scan.

The original image generation means 25 reads out the photoacoustic signals from the receiving memory 23, and generates a photoacoustic image (a third photoacoustic image) based on the readout photoacoustic signals. For example, the original image generation means 25 generates a third photoacoustic image of a cross section at an arbitrary position by generating photoacoustic three-dimensional image data from three-dimensional data of photoacoustic signals, and by combining tomographic images for a predetermined number of cross sections in the vicinity of the position of the cross section to be imaged. The original image generation means 25 generates a tomographic image (a third photoacoustic image) in a cross section parallel to a sonic wave detection surface of the probe 11 by combining tomographic images for a predetermined thickness. When the plural images are combined together as a tomographic image, for example, even if the position of a blood vessel in a direction perpendicular to the sonic wave detection surface changes, it is possible to keep the changing blood vessel within a tomographic image.

The first filter means 26 generates a low frequency image corresponding to a frequency component of, for example, 5 MHz or less by applying, to the third photoacoustic image generated by the original image generation means 25, a low-pass filter that selectively transmits a frequency component of 5 MHz or less (step S3). The second filter means 27 generates a high frequency image corresponding to a frequency component of, for example, higher than 5 MHz by applying, to the third photoacoustic image generated by the original image generation means 25, a high-pass filter that selectively transmits a frequency component higher than 5 MHz (step S4).

The image combination means 28 combines the low frequency image and the high frequency image together by placing, on a pixel the pixel value of which is less than or equal to a threshold in the low frequency image, a corresponding pixel in the high frequency image (step S5). For example, the image combination means 28 judges a pixel (area) the pixel value of which is less than or equal to a threshold in the low frequency image. Further, the image combination means 28 combines the high frequency image and the low frequency image together by addition after changing the pixel values of pixels in an area other than a corresponding area of the high frequency image to 0 (black). It is desirable that a user can arbitrarily set the threshold used to combine images. When the images are combined, different colors may be assigned to the low frequency image and the high frequency image, and the images may be combined. In such a case, a user can identify parts derived from the low frequency image and parts derived from the high frequency image.

In the embodiments of the present invention, the low frequency image and the high frequency image are combined together by generating a photoacoustic image of a low frequency component and a photoacoustic image of a high frequency component, and by placing, on a pixel the pixel value of which is less than or equal to a threshold in the low frequency image, a corresponding pixel in the high frequency image. When the images are combined in this manner, it is possible to compensate a part of the low frequency image without information or with a small amount of information by information in the high frequency image. Consequently, observation of information about details becomes possible while observation of a blood vessel with a specific diameter becomes easy. In the embodiment of the present invention, the high frequency image is not placed in an area of the low frequency image in which pixel values are larger than the threshold, in other words, an area in which a target of measurement is recognizable in the low frequency image. Therefore, it is possible to provide an image with excellent recognition characteristics in which scatter of bright fragments is suppressed, compared with a case in which the low frequency image and the high frequency image are simply placed one on the other in the whole area.

In the embodiment of the present invention, the laser unit 13 may output light in plural different wavelengths to the subject to be examined. Further, the probe 11 may detect photoacoustic waves induced in the subject to be examined after the light in each of the plural different wavelengths has been illuminated the subject to be examined. In that case, the image generation means 24 may generate, based on detected photoacoustic signals corresponding to light in the plural wavelengths, a low frequency image and a high frequency image corresponding to each of the plural wavelengths. For example, light in a first wavelength and light in a second wavelength may be output to the subject to be examined, and a low frequency image and a high frequency image may be generated for each of the first wavelength and the second wavelength. For example, the first wavelength may be a wavelength appropriate for imaging blood (blood vessels), and the second wavelength may be a wavelength appropriate for imaging a chemical agent (a contrast medium). Alternatively, the first wavelength may be the wavelength of an isosbestic point of hemoglobin, and the second wavelength may be a wavelength corresponding to a peak of deoxyhemoglobin.

When a target of imaging at the first wavelength and a target of imaging at the second wavelength differ from each other, as described above, the cut-off frequency of the low-pass filter and the cut-off frequency of the high-pass filter applied to the third photoacoustic image in the first filter means 26 and the second filter means 27 may be changed based on the wavelengths. Generally, the diameter of arteries is larger than the diameter of veins. When frequencies (the cut-off frequency of the low-pass filter and the cut-off frequency of the high-pass filter) that are boundaries between a low frequency and a high frequency are changed for a photoacoustic image corresponding to the first wavelength and a photoacoustic image corresponding to the second wavelength, it is possible to easily observe arteries and veins at each of the wavelengths.

Figure 10:
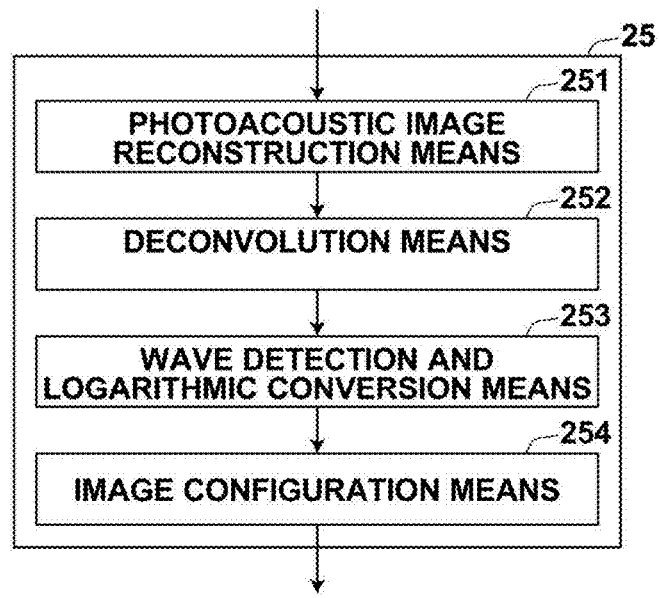
FIG. 10 is a block diagram illustrating an original image generation means in a photoacoustic image generation apparatus according to a second embodiment of the present invention.

Next, a second embodiment of the present invention will be described. FIG. 10 is a diagram illustrating the configuration of the original image generation means 25 in a photoacoustic image generation apparatus (an ultrasonic unit 12) in the second embodiment of the present invention. The original image generation means 25 includes a photoacoustic image reconstruction means 251, a deconvolution means 252, a wave detection and logarithmic transform means 253 and an image configuration means 254. The structure other than the original image construction means 25 may be similar to the photoacoustic image generation system 10 in the first embodiment, illustrated in FIG. 1.

The photoacoustic image reconstruction means 251 reconstructs photoacoustic signals. The deconvolution means 252 generates deconvoluted signals from the photoacoustic signals reconstructed by the photoacoustic image reconstruction means 251. The deconvolution means 252 generates the deconvoluted signals by deconvoluting a differential waveform of light, which is a differential waveform of a temporal waveform of the light intensity of light with which the subject to be examined has been illuminated. The wave detection and logarithmic transform means 253 performs wave detection and logarithmic transform on the signals generated by deconvoluting the differential waveform of light. The image configuration means 254 generates a third photoacoustic image based on the signals on which wave detection and logarithmic transform has been performed.

The deconvolution means 252 converts the reconstructed photoacoustic signals from time domain signals to frequency domain signals, for example, by discrete Fourier transform. Further, the deconvolution means 252 converts the differential waveform of light from a time domain signal to a frequency domain signal by discrete Fourier transform. The deconvolution means 252 calculates, as an inverse filter, an inverse of the differential waveform of light on which Fourier transform has been performed. Further, the deconvolution means 252 applies the inverse filter to photoacoustic signals in the frequency domain on which Fourier transform has been performed. When the inverse filter is applied, the differential waveform of light is deconvoluted in the frequency domain signals. After then, the photoacoustic signals to which the inverse filter has been applied is converted from frequency domain signals to time domain signals by inverse Fourier transform.

Deconvolution of differential waveform of light will be described. Micro absorptive particles, which are light absorption substance, will be considered, and a state of inducing a pressure wave (photoacoustic pressure wave) by absorption of pulsed laser light by the micro absorptive particles will be considered. When time is t and a photoacoustic pressure wave induced from a micro absorptive particle at position r is observed at position R, pressure waveform $p_{micro}$ (R, t) is the following spherical wave according to [I. G. Calasso et al., "Photoacoustic Point Source", PHYSICAL REVIEW LETTERS, Vol. 86, No. 16, pp. 3550-3553, 2001]:

[Number 1]

$$p_{micro}(R, t) = \frac{k}{|r-R|} \frac{d}{d\left(t - \frac{|r-R|}{v_s}\right)} I\left(t - \frac{|r-R|}{v_s}\right)$$

Here, I(t) represents a temporal waveform of the light intensity of excitation light, and coefficient k is a conversion coefficient when a particle absorbs light and outputs an acoustic wave. Further, $v_s$ is sound speed in the subject to be examined, and positions r, R are vectors representing positions in space. Pressure induced from the micro absorptive particle is a spherical wave proportional to the differential waveform of light pulse, as shown in the above expression:

A pressure waveform actually obtained from an object to be imaged is considered to be a waveform in which the aforementioned micro absorption waveforms are superposed one on another (superposition principle) because the absorptive substance in the object to be imaged is more macro-sized. Here, it is assumed that the absorption distribution of particles outputting macro photoacoustic waves is A(r-R), and that an observed waveform of pressure from the macro absorptive substance is $p_{macro}$ (R, t). At observation position R, a photoacoustic wave from an absorptive particle located at radius $v_s t$ from observation position R is observed at each of time. Therefore, observed waveform $p_{macro}$ (R, t) is expressed by the following pressure waveform equation:

[Number 2]

$$p_{macro}(R, t) = \iiint A(r-R) \times \frac{k}{|r-R|} \frac{d}{d\left(t - \frac{|r-R|}{v_s}\right)} \quad (1)$$

$$I\left(t - \frac{|r-R|}{v_s}\right) dV$$

$$= \int_0^\pi \int_{-\frac{\pi}{2}}^{\frac{\pi}{2}} \int_0^{|r-R|=v_s t} \frac{kA(r-R)}{|r-R|} I'\left(t - \frac{|r-R|}{v_s}\right)$$

$$|r-R|^2 \sin\theta \, d|r-R| d\theta d\phi$$

$$= \int_0^{|r-R|=v_s t} \frac{k}{|r-R|} \int_0^\pi \int_{-\frac{\pi}{2}}^{\frac{\pi}{2}} A(r-R) dS \times I'\left(t - \frac{|r-R|}{v_s}\right)$$

$$= d|r-R|\left[\frac{k}{|r-R|}\int_0^\pi \int_{-\frac{\pi}{2}}^{\frac{\pi}{2}} A(r-R) dS\right] * \left[I'\left(t - \frac{|r-R|}{v_s}\right)\right]$$

As the above equation (1) shows, the observed waveform represents a convolution type of light pulse differential. When the differential waveform of light pulse is deconvoluted from the observed waveform, the distribution of absorptive substance is obtainable. In the above descriptions, a case in which differential waveform of light is deconvoluted from the reconstructed photoacoustic signals was described. Alternatively, differential waveform of light may be deconvoluted from the photoacoustic signals that have not been reconstructed.

In the embodiment of the present invention, the differential waveform of light with which the subject to be examined has been illuminated is deconvoluted from the detected photoacoustic signals. Since the differential waveform of light is deconvoluted, the distribution of light absorptive substance is obtainable, and an absorption distribution image is generatable. When processing similar to the first embodiment is performed after imaging the distribution of absorptive substance, it is possible to more clearly recognize the position of blood vessels or the like in a combination image of the low frequency image and the high frequency image. Other advantageous effects are similar to the first embodiment.

In each of the aforementioned embodiments, a case of imaging a blood vessel part was mainly described. However, the present invention is not limited to this example. For example, a tubular structure, such as nerves or lymphatic vessels, may be imaged. In the first embodiment, a case in which volume data are generated, and an arbitrary tomographic image is generated from the volume data, and a low frequency image and a high frequency image are generated from the tomographic image was mainly described. However, the present invention is not limited to this example.

In each of the aforementioned embodiments, a photoacoustic image including both of a frequency component less than or equal to a predetermined frequency and a frequency component higher than a predetermined frequency is temporarily generated. After then, a low frequency image and a high frequency image are generated by application of a low-pass filter and a high-pass filter to the photoacoustic image. However, the present invention is not limited to this example. Instead of applying the low-pass filter and the high-pass filter to the photoacoustic image including both of the frequency components, or in addition to this, a low-pass filter and a high-pass filter may be applied to photoacoustic signals before generation of an image to divide the photoacoustic signals into a low frequency component and a high frequency component. Then, a first photoacoustic image and a second photoacoustic image may be generated based on the low frequency component and the high frequency component.

So far, the present invention has been described based on preferable embodiments. However, the photoacoustic image generation apparatus, system and method of the present invention is not limited to the aforementioned embodiments. Various modifications and changes are possible without departing from the scope of the present invention.

What is claimed is:

1. A photoacoustic image generation system comprising:
   a light source that outputs light with which a subject to be examined is illuminated;
   a photoacoustic wave detection unit that detects a photoacoustic wave induced in the subject to be examined by illumination of the subject to be examined with the light; and
   a photoacoustic image generation apparatus that generates photoacoustic images of the subject using a detection signal of the detected photoacoustic wave,
   wherein the photoacoustic image generation apparatus generates:
      a first photoacoustic image of the subject from the detection signal, the first photoacoustic image corresponding to a frequency in a range of 5 Mhz or less component less than or equal to a first frequency, and
      a second photoacoustic image of the subject from the detection signal,
      the second photoacoustic image corresponding to a frequency component higher than the first frequency, and
   wherein the photoacoustic image generation apparatus combines the first photoacoustic image and the second photoacoustic image together by placing, on a pixel in the first photoacoustic image the pixel value of which is less than or equal to a threshold, a pixel in the second photoacoustic image corresponding to the pixel in the first photoacoustic image,
   and the photoacoustic image generation apparatus generates the first photoacoustic image by applying a low-pass filter that at least attenuates a component of higher than the first frequency to the third photoacoustic image, and generates the second photoacoustic image by applying a high-pass filter that at least attenuates a component of less than or equal to the first frequency to the third photoacoustic image.

2. The photoacoustic image generation system, as defined in claim 1, wherein the photoacoustic image generation apparatus generates
   a third photoacoustic image using the detection signal of the photoacoustic wave before generating the first and second photoacoustic images, wherein the third photoacoustic image includes both of: (i) the frequency component less than or equal to the first frequency; and (ii) the frequency component higher than the first frequency.

3. The photoacoustic image generation system, as defined in claim 2, wherein the photoacoustic image generation apparatus further obtains, from three-dimensional image data generated from a three-dimensionally detected photoacoustic wave, a cross section by cutting along a plane perpendicular to an axis which is one of axes constituting three-dimensional space, and generates, as the third photoacoustic image, a tomographic image in which image data of plural cross section images in a predetermined range in a direction along the axis are combined, wherein the predetermined range includes the cross section obtained by cutting.

4. The photoacoustic image generation system, as defined in claim 3, wherein the photoacoustic image generation apparatus generates a plurality of tomographic images by obtaining cross sections by cutting at a plurality of positions along the axis.

5. The photoacoustic image generation system, as defined in claim 4, wherein the photoacoustic image generation apparatus obtains the cross sections by cutting at regular intervals.

6. The photoacoustic image generation system, as defined in claim 3, wherein the photoacoustic image generation apparatus obtains, along the axis corresponding to a depth direction of the subject to be examined, the cross section by cutting in a direction parallel to a photoacoustic wave detection surface during detection of the photoacoustic wave.

7. The photoacoustic image generation system, as defined in claim 3, wherein the photoacoustic image generation apparatus combines the image data in the predetermined range by projecting a maximum value of the image data in the predetermined range or by calculating the integral of the image data in the predetermined range.

8. The photoacoustic image generation system, as defined in claim 1, wherein the photoacoustic image generation apparatus combines the first photoacoustic image and the second photoacoustic image after assigning different colors to them.

9. The photoacoustic image generation system, as defined in claim 1, wherein the photoacoustic image generation apparatus
deconvolutes, from the detection signal of the photoacoustic wave, a differential waveform of the light with which the subject to be examined has been illuminated.

10. A photoacoustic image generation method comprising the steps of:
generating photoacoustic images using a detection signal of a photoacoustic wave induced in a subject to be examined by illumination of the subject to be examined with light, wherein a first photoacoustic image corresponding to a frequency component less than or equal to a first frequency in a range of 5 Mhz or less and a second photoacoustic image corresponding to a frequency component higher than the first frequency are generated;
combining the first photoacoustic image and the second photoacoustic image together by placing, on a pixel in the first photoacoustic image the pixel value of which is less than or equal to a threshold, a pixel in the second photoacoustic image corresponding to the pixel in the first photoacoustic image, and
wherein the first photoacoustic image is generated by applying a low-pass filter that at least attenuates a component of higher than the first frequency to the third photoacoustic image; and
the second photoacoustic image is generated by applying a high-pass filter that at least attenuates a component of less than or equal to the first frequency to the third photoacoustic image.

11. The method according to claim 10, wherein:
in the step of generating photoacoustic images, before generating the first and second photoacoustic images, a third photoacoustic image is generated using the detection signal of the photoacoustic wave.

* * * * *